United States Patent [19]
Thirumalachar et al.

[11] Patent Number: 6,015,808
[45] Date of Patent: Jan. 18, 2000

[54] SYNTHESIS OF PHARMACEUTICAL COMPOSITIONS WITH LACTAMS AND β-LACTAMS/OXO THIA AZABICYCLO COMPOUNDS

[76] Inventors: Mandayam Jeersannidhi Thirumalachar; Mandayam Jeersannidhi Narasimhan, Jr., both of P.O. Box 506, Locust St., Walnut Creek, Calif. 94596

[21] Appl. No.: 08/517,964

[22] Filed: Aug. 22, 1995

Related U.S. Application Data

[63] Continuation of application No. 08/109,353, Aug. 20, 1993, abandoned.

[51] Int. Cl.⁷ .......................... A61K 31/43; C12P 17/00; C07D 499/00
[52] U.S. Cl. .......................... 514/192; 514/183; 514/200; 514/359; 514/430; 514/438; 514/444; 435/117; 435/128; 435/130; 424/114; 540/304; 549/29; 549/32
[58] Field of Search ........................... 424/114; 514/183, 514/359, 366, 192, 367, 430, 438, 444, 200, 99; 435/43, 41, 117, 118, 128, 130

[56] References Cited

U.S. PATENT DOCUMENTS 4,508,723   4/1985   Schaffner et al. ...................... 514/195

*Primary Examiner*—Keith D. MacMillan
*Assistant Examiner*—P. Ponnaluri
*Attorney, Agent, or Firm*—Cheryl L. Farine

[57] ABSTRACT

Pharmaceutical compositions with heretofore unknown and enhanced physical, chemical, and biological properties are prepared by combining known biologically active parent compounds with oxo thia azabicyclo compounds, such as lactam and β-lactam compounds, capable of rapidly transporting the parent compounds in undegraded form to their target sites of action. A process for combining the parent compound with β-lactam compounds consists of dissolving the parent compound in a polar solvent, adding a β-lactam compound, incubating the resulting mixture, followed by drying, and subjecting the remaining solid material to solvent washing or extraction to further purify the new pharmaceutical composition. The new pharmaceutical composition possesses the biological and therapeutic activity of the parent compound and the barrier penetrating characteristics of the β-lactam compound, which results in improved pharmacodynamics, including bioavailability, and an improved chemotherapeutic index, such that lower amounts of the parent may be used to avoid the toxic effects of the parent compound. Some of the new pharmaceutical compounds provide for the first time parent compounds in an orally administerable form.

6 Claims, No Drawings

SYNTHESIS OF PHARMACEUTICAL COMPOSITIONS WITH LACTAMS AND β-LACTAMS/OXO THIA AZABICYCLO COMPOUNDS

This application is a continuation Ser. No. 08/109,353, field Aug. 20, 1993, now abandoned.

FIELD OF THE INVENTION

This invention relates to novel pharmaceutical compositions, and a process for preparing such compositions, by combining known, biologically active parent compounds with other compounds capable of rapidly transporting the parent compounds in undegraded form to their respective target sites in a mammalian host. More particularly, this invention relates to pharmaceutical compositions prepared by combining known biologically active parent compounds, such as anticancer, antibacterial, antiviral, antifungal, antiparasitic, antiparkinsonian, neuromuscular, neuroleptic, antiarthritic, cardiovascular, pulmonic, renogenic, hepatogenic, lymphogenic or hormonal compounds, or insulin, with one or more molecules of an oxo thia azabicyclo compound, such as a lactam or β-lactam compound, said compound acting as a carrier or umbrella to protect the parent compound from degrading before it reaches its target site, thus assuring delivery into that site.

It has been found that the pharmaceutical compositions of this invention possess heretofore unknown and enhanced physical, chemical and biological properties, which results in improved pharmacodynamics, including bioavailability, and an improved chemotherapeutic index, when compared to those of the parent compounds alone. As such, the methods, compositions and applications of this invention may overcome many of the therapeutic disadvantages currently being encountered with the use of the parent compounds alone.

BACKGROUND OF THE INVENTION

It is recognized that the use of certain therapeutic compounds, including anticancer, antibacterial, antiviral and antifungal compounds, is limited by inherent, toxic side effects, which at times may be irreversible and severe. The delivery of such compounds directly to their target sites of action is thus desirable, in order to avoid the toxic effects of systemic administration, which often counter the therapeutic effects sought to be achieved.

The use of certain therapeutic compounds is further limited, in many instances, because the compound may be degraded by natural metabolic processes, before it can reach its target site of action. As a result, much higher doses must be given to assure that an adequate amount of the therapeutic compound is available at the target site of action to elicit the desired response. Administration of these higher does may also result in toxic side effects, in addition to the inherent toxic effects already mentioned.

Methods to deliver such compounds to their target sites in a relatively undegraded form and in smaller amounts are, therefore, highly desirable. Rapid transport of therapeutic compounds directly to target sites avoids undue degradation and the systemic toxic effects associated with the use of these compounds, primarily because the dosage necessary to obtain the therapeutic effect can be reduced, thus reducing the effective amount of the compound in the systemic circulation.

It is further recognized that the use of certain therapeutic compounds is limited, because many of these compounds are not available in orally administerable forms, or are poorly absorbed orally. Thus, the only recourse is either to administer the compound parenterally, which may require hospitalization or expensive, outpatient intramuscular or intravenous therapy, or to treat a patient with a less desirable orally administerable compound. Neither of the foregoing options is optimal.

It is known in the art that oxo thia azabicyclo compounds, particularly β-lactam compounds, possess certain superior pharmacokinetic properties which permit rapid and complete passage through host barriers, such as the G.I. tract, intestines, and other mucous membrane barriers; tissue barriers, such as the blood vessels, lymph nodes and others; cellular membrane barriers and intracellular barriers, such as the endoplasmic reticulum, mitochondria, nuclear membranes, and the nucleus itself. Likewise, the pharmacokinetic properties of such compounds also allow rapid and complete passage through the external and internal barriers of pathogen cells, including microorganisms and cancer cells.

Second, it is known that β-lactam compounds are chemically reactive, because of the ring strain inherent in the β-lactam ring. (Kirk-Othmer, Chem Tech. Encyclopedia, p. 881 (1984)). The geometry of the β-lactam ring, with its accompanying increased ring strain, accounts for the greater reactivity of β-lactam antibiotics. Ring-opening reactions take place under the influence of chemical reagents.

For example, the β-lactam ring readily opens on reaction with various nucleophiles. After ring opening, β-lactam compounds may undergo molecular rearrangement to form new compounds. Synthesis of various heterocyclic compounds, derived from strategically substituted β-lactam compounds, via β-lactam ring opening and intramolecular rearrangement, have been described in the literature. Manhas, M. S., Amin, S. G., and Bose, A. K., *Heterocycles* (1976), 5, 669. Manhas et al. describes the formation of compositions, such as carbostyril, coumarin, diazepin, thiazepin, etc., formed entirely by opening the β-lactam ring, followed by intramolecular rearrangement of the β-lactam compound itself. None of these compositions is used medically. Manhas et al. does not describe or disclose the preparation of useful pharmaceutical compositions by the use of β-lactam ring opening and intramolecular rearrangement, followed by reclosing of the ring. Manhas et al. accomplishes intentional β-lactam ring opening through vigorous chemical reactions, resulting in the complete breakdown of the fused β-lactam ring.

Further, Manhas et al. does not describe or disclose a process for combining β-lactam compounds with other biologically active parent compounds to form new compositions, which are equal in activity to the parent compound, but less toxic due to the lower amount of the parent compound contained in, and the improved pharmacodynamics of, the new composition. The compositions taught by Manhas et al. are formed entirely by β-lactam ring-opening and intramolecuar rearrangement of the β-lactam compound itself. No other compounds are added to, or contemplated for, the process described by Manhas et al.

It has been shown that the use of milder conditions may accomplish opening of the β-lactam ring, followed by subsequent reclosing of the ring, without a complete breakdown of the β-lactam ring structure. In addition, prior studies have shown that under certain conditions, wherein the β-lactam ring is opened and reclosed, β-lactam compounds, such as penicillin, may polymerize to form low molecular weight peptides. (Grant, Clark & Alburn, *J.Am.Chem.Soc.* 84, 876 (1962)). These studies were conducted in water, with the hydroxyl (—OH) group acting as the nucleophile. The resultant peptides were composed entirely of β-lactam units and were biologically inactive.

Various sites on the β-lactam penicillin molecule, where ring opening may take place, have been reported in the art. (Stoodley, R. J. et al., *Tetrahedron Letters*, 1205 (1966); Kitchin, J. & Stoodley, R. J., *J.Chem Soc.*, 2460 (1973). For example, attack by nucleophiles and electrophiles on the carbonyl group of the β-lactam ring results in ring opening. (Clarke, H. T., et al., *Chemistry of Penicillin*, Princeton University Press, Princeton, N.J. (1949)). Specifically, hydroxyl (—OH) groups, acting as nucleophiles, can attack the β-lactam compound at the carbonyl site, resulting in the opening of the β-lactam ring. (Wilson, Gisvold, Doerge, *Textbook Org. Med. Pharm. Chem.*, 7th ed., pp. 276–77). Ring opening and intramolecular rearrangement, facilitated by nucleophilic attack, have also been reported by Morin, et al., *J.Chem.Soc.* 21, 1401 (1969).

Finally, it is known that compounds containing terminal amino ($NH_2$) groups are capable of reacting and forming ionic and covalent bonds with themselves and with other molecules to form polymers known as polypeptides. These terminal amino groups will combine with other compounds at available receptor sites. The reaction consists of nucleophilic attack on a receptor site of another compound by the primary amino group of the terminal-amino-group-containing compound, with the resultant formation of polyamides of various chain lengths.

Compounds containing terminal amino groups are well known compounds in the art. Among the biologically active therapeutic compounds containing such groups are certain anticancer, antiviral, antifungal, antibacterial, antiparasitic, antiparkinsonian, neuromuscular, neuroleptic, antiarthritic, cardiovascular, pulmonic, renogenic, hepatogenic, lymphogenic, and hormonal compounds, including certain steroidal and endocrine compounds, and insulin. The therapeutic use of these known compounds often requires the administration of high doses to achieve the intended therapeutic effect, often resulting in serious toxic side effects or complications. In many instances, these compounds cannot be administered orally, or are poorly absorbed orally.

Oxo thia azabicyclo compounds, including the lactams and β-lactam compounds, are also well-known in the art. Among the naturally occurring β-lactam compounds are antibiotics such as penicillins, cepalosporins, cephamycins, cephems, penams, monobactams, and nocardicins, to name a few. There are, of course, countless other lactams and β-lactam compounds, which are believed to be useful in the present invention. The essential feature is the presence of the β-lactam ring, which is amenable to nucleophilic attack, resulting in opening of the β-lactam ring, followed by intramolecular rearrangement, and ring reclosing.

It is one object of the present invention to produce useful, pharmaceutical compositions, prepared by combining biologically active parent compounds with β-lactam compounds in a manner heretofore unknown, which are highly efficacious at lower doses and less toxic than the parent compounds when used alone.

It is a further object of this invention to provide a process for combining a biologically active parent compound with a β-lactam compound.

It is yet a further object of the invention to produce useful, pharmaceutical compositions which are capable of rapidly delivering parent compounds relatively undegraded to their target sites.

Still another object of the invention is to provide orally administerable pharmaceutical compositions, which have the same therapeutic activity at lower doses and less toxicity than the parent compound from which they were derived.

Such objects and further advantages of the invention will be apparent from the detailed description which follows.

SUMMARY OF THE INVENTION

The present invention concerns pharmaceutical compositions, prepared by combining biologically active parent compounds with β-lactam compounds, the β-lactam compounds acting as carriers, or umbrellas, to protect the parent compounds from degradation and to assure their rapid and complete delivery to their respective target sites. These pharmaceutical compositions possess enhanced biological activity at lower doses than those previously known for the parent compound alone, and are less toxic. In some cases, these pharmaceutical compositions may be administered orally, unlike the parent compound.

The present invention also concerns a process for producing such compositions, comprising the steps of dissolving a biologically active parent compound having a terminal amino group in a solvent to the point of saturation; adding a β-lactam compound to the parent compound/solvent solution to the point of saturation; incubating the resultant solution at room temperature or lower for six to twelve hours, during which it is believed that a reaction of the ring-opened β-lactam compound with the parent compound occurs. After incubation, the solution is centrifuged or filtered as needed, and then evaporated to obtain a solid material. The solid material, which is, in essence, the new pharmaceutical composition, is then dissolved in a differential, solvent to remove any unreacted or excess parent or β-lactam compounds, which are insoluble in the selected solvent, followed by centrifuging or filtering as needed. The solution is then evaporated to dryness. The remaining material is then washed with a suitable solvent to purify the new pharmaceutical composition, which is then dried and stored.

DETAILED DESCRIPTION OF THE INVENTION

The present invention is predicated on the combination of an oxo thia azabicyclo compound, such as a lactam or β-lactam compound, with a biologically active parent compound having terminal amino groups. Specifically, penicillin and other β-lactam compounds contain specific peripheral sites capable of reacting with terminal amino groups, ie., (—$NH_2$) groups, to form thiols, amides, and Schiff's bases. In addition, once the β-lactam ring is opened, terminal amino groups may also incorporate themselves into the opened β-lactam ring. While the exact mechanism is not known, it is believed that the parent compound, through its terminal amino groups, reacts with the ring-opened β-lactam compound at peripheral receptor sites and incorporates into the ring itself, to form a single entity pharmaceutical composition. The resultant pharmaceutical compositions are believed to be single entity reaction products, which exhibit unexpectedly superior bioavailability, unexpected efficacy and less toxicity than that previously seen with the parent compound alone.

The pharmaceutical compositions of the present invention are produced by dissolving a biologically active parent compound having a terminal amino group in a polar solvent, in particular, a hydro-alcoholic solution; adding a β-lactam compound to the parent compound/solvent solution to the point of saturation; and incubating the resultant solution at room temperature or lower for six to twelve hours, where it is believed that a reaction of the β-lactam compound and parent compound takes place. After incubating, the solution is centrifuged or filtered as needed, and then evaporated to dryness. The remaining solid material, which is in essence the new pharmaceutical composition, is dissolved in a differential, polar solvent to remove any unreacted or excess β-lactam or parent compounds, which are insoluble in the selected solvent, followed by centrifuging or filtering as needed. The solution is then evaporated to dryness. The remaining material is then extracted by washing with solvents, to further purify the new pharmaceutical composition, which is then dried and stored.

As used herein, the phrase "pharmaceutical composition" includes the product resulting from the combination of a β-lactam compound with a biologically active parent compound, wherein the terminal amino (—$NH_2$) groups of the parent compound combine, or react, with the peripheral —$NH_2$ receptor sites of the β-lactam compound or incorporate into the opened β-lactam ring, followed by ring closing, or both.

As used herein, the phrase "β-lactam compound" includes oxo thia azabicyclo compounds, specifically lactams and β-lactam compounds, such as the penicillins, including sodium penicillin G, also known as benzyl penicillin, potassium penicillin V, also known as phenoxymethyl penicillin; cephalosporins, such as cephalexin; penams; cephamycins; cephams; monobactams; and nocardicins, all of which contain a β-lactam ring and peripheral sites at which reaction with the terminal amino groups of a biologically active parent compound may occur.

As used herein, the phrase "polar solvent" includes methanol, ethanol, propanol, and other alcohols, water, and all combinations thereof, i.e., hydroalcoholic solutions, all of which contain a hydroxyl (—OH) group capable of attacking and opening the β-lactam ring. Other polar solvents, which are known in the art to act as nucleophiles, may also attack and open the β-lactam ring and thus fall within the scope of this invention.

As used herein, the phrase "differential solvent" includes solvents, such as acetone, which are capable of separating the new pharmaceutical composition from any unreacted or excess parent or β-lactam compound on the basis of solubility. The differential solvent selected should be capable of dissolving the new pharmaceutical composition, while leaving behind unreacted, or excess, parent compound or β-lactam compound, which should be insoluble in the selected solvent.

As used herein, the phrase "parent compound" includes biologically active or therapeutic compounds, such as anticancer, antifungal, antibacterial, antiviral, antiparasitic, antiparkinsonian, neuroleptic, neuromuscular, antiarthritic, cardiovascular, pulmonic, renogenic, hepatogenic, lymphogenic and hormonal compounds, including steroidal and endocrine compounds, and insulin, all of which are already known in the art and which contain terminal amino (—$NH_2$) groups capable of combining with peripheral receptor sites on β-lactam compounds or incorporating into an opened β-lactam ring.

Parent compounds useful in the practice of the present invention include the anticancer compounds, represented by the following: bleomycin, daunorubicin, adriamycin, mitomycin-C, mithramycin, and actinomycin-D (dactinomycin). Parent compounds also include the antiviral compounds, represented by AZT, also known as zidovudine, and formerly known as azidothymidine, acyclovir, gancyclovir, and amantadine HCl. Parent compounds further include the antifungal antibiotics, represented by aureofungin, amphotericin B, fhamycin, nystatin, polyene, clotrimazole, imidazole, ketaconazole and other azole compounds. Parent compounds further include the antibacterial antibiotics, represented by the aminoglycoside antibiotics, such as gentamicin, tobramycin, amikacin, paromomycin, streptomycin, spectinomycin, neomycin and kanamycin, and chloramphenicol and quinolone compounds. Parent compounds further include the antiparasitic antibiotics, represented by antiamoebin, avernictum and antiprotozoin. Parent compounds further include antiparkinsonian and neuromuscular compounds, represented by pimprinine. Parent compounds further include hormonal compounds, including steroidal or endocrine compounds, represented by hydrocortisone, prednisone, and prednisolone; proteins, carbo-proteins and steroids, having a cyclopentano perhydro phenanthrene (CPPP) nucleus; human growth hormone; prolactin; estrogens; testosterone; vasopressin; ACTH; thyroxin; glucagon and insulin. Parent compounds further include antiarthritic compounds, represented by naproxen and indomethacin. Parent compounds further include cardiovascular drugs, represented by digitalis, digoxin, digitoxin, digitonin, lanatoside C, TPA, streptokinase, urokinase and protease-inhibitors. Parent compounds further include renogenic compounds represented by furosemide.

Generally, the parent compounds of the present invention combine with the β-lactam compounds in a ratio of greater than 1 part of the parent compound to 10 parts of the β-lactam compound (1:10); however, certain combinations with ratios of 1:4 have been found to be efficacious as well and are considered to be within the scope of the invention. There is no fixed or preferred ratio; the ratio is determined by the number of terminal amino groups on the parent compound that are available for reacting with specific receptor sites on the β-lactam compound or incorporating into the opened β-lactam ring, the number of such receptor sites on the particular β-lactam compound selected, and the amount of parent compound or β-lactam compounds used.

β-lactam compounds, particularly β-lactam antibiotics, possess excellent host and pathogen barrier penetrating properties. It is believed that the β-lactam compound retains its barrier penetrating properties even after the β-lactam ring is opened, undergoes intramolecular rearrangement and then closes.

In the present invention, although not wishing to be limited by theory, it is believed that the β-lactam ring is opened in the presence of a parent compound dissolved in methanol, that the terminal amino groups of the parent compound combine with peripheral receptor sites on the β-lactam compound and incorporate into the opened β-lactam ring, followed by ring-closure, resulting in the formation of a single entity pharmaceutical composition. On combining with the β-lactam compound in this manner, the parent compound acquires the barrier penetrating properties of the β-lactam compound, while retaining its own biological activity. The β-lactam compound thus acts as a carrier for the attached parent compound to assure passage through various host and pathogen barriers and thus, the rapid and complete distribution of the parent compound to the target site with minimal degradation and loss of activity.

The process described herein involves the use of a polar solvent, such as methanol, ethanol, propanol, and other alcohols, or water, and all combinations thereof, i.e., hydroalcoholic solutions, most preferably of methanol, to facilitate the combination of the β-lactam compound with the parent compound. The parent compound is initially dissolved in the polar solvent, which it is believed causes the parent compound to ionize. The β-lactam compound, most preferably a penicillin, is next added to the solution to the point of saturation, and the resultant solution is incubated at room temperature or lower (0° C.–24° C.) for six to twelve hours, during which it is believed that the β-lactam ring opens, and the terminal amino groups of the parent compound combine with the peripheral receptor sites on the β-lactam compound or incorporate into the opened β-lactam ring. The β-lactam ring then closes, resulting in the formation of a new, single entity pharmaceutical composition.

Following formation of the pharmaceutical composition, the solution is centrifuged or filtered as needed, then evaporated to a solid material, which is in essence the new pharmaceutical composition. The solid material is then dissolved in a differential solvent, usually acetone, to ensure removal of any unreacted or excess β-lactam or parent compounds, which are insoluble in the differential solvent, followed by filtering and centrifuging as needed. Acetone is one such solvent which leaves behind unreacted β-lactam compound. The solution is then evaporated to dryness, and the remaining material is washed with solvents, most preferably petroleum ether or hexanes, to purify the new pharmaceutical composition, which is then dried and stored.

The physical form of the parent compound is not critical, provided that it is soluble in the selected polar solvent. The amount of the parent compound should be sufficient to assure complete reaction of the parent compound with the β-lactam compound, in order to achieve the full advantages and benefits of the invention. The degree to which the parent compound will react with the β-lactam compound at any pH will depend to some extent on the number of available receptor sites on the selected β-lactam compound and the number of terminal amino groups on the parent compound available for reaction.

As a general rule, the ratio of the parent compound to β-lactam compound is usually at least 1:10; however, ratios may range from about 1:10 to 1:40. Depending on the number of terminal amino groups on the parent compound available for reaction, a ratio of 1:4 may be sufficient. No fixed ratio is contemplated by this invention.

According to the results of HPLC studies, it is believed that the above described process for combining a β-lactam compound with a parent compound, using polar solvents, produces a single structure pharmaceutical composition with unexpectedly enhanced pharmacological activity over the single parent compound previously known in the art. It is further believed that the pharmaceutical composition is formed by an irreversible chemical combination of the parent compound and β-lactam compound. The chemical modification of the pharmaceutical composition is shown by changes in several physical and chemical analytical parameters, including change in solubility of the pharmaceutical composition over the parent compound, change in chromophore, and changes in different types of chromatograms, particularly HPLC, to reflect a single entity pharmaceutical composition, instead of two individual compounds.

In addition, biological activity of the pharmaceutical compositions show changes over that of the parent compounds alone. significant changes in in vitro and in vivo cure rates have been noted, even though the parent compound/β-lactam compound ratio reveals that the parent compound is present in far lower amounts than normally recommended or required for the parent compound alone to effectuate a cure. This unexpected improvement in cure rates is believed to occur, because the pharmaceutical compositions cross certain physiological barriers, such as the blood-brain or blood-placenta barrier, as well as cellular barriers, to reach the target site of infection or inflammation, whereas the parent compound could not cross these barriers alone.

The toxicity of the pharmaceutical composition is also significantly decreased, as compared to the parent compound alone. Several parent compounds described herein are extremely nephrotoxic (toxic to the kidney), due to elimination through the renal (kidney) system. The pharmaceutical compositions appear to have lowered renal toxicity, due to the reduction in the needed amounts of the parent compounds when combined with the β-lactam compound, as compared to the parent compound alone. Liver toxicity may also be reduced for the same reason, because there is less parent compound to be metabolized by the hepatic system.

Previously, parent compounds were used for their pharmacological or therapeutic activity, but were often limited by the toxic effects inherent in such compounds. As shown in the examples, because the pharmaceutical compositions of the invention have enhanced pharmacodynamic activity, including improved bioavailability, through more rapid and targeted distribution, the effective dosage may be significantly decreased for all modes of administration.

The pharmaceutical compositions of the invention have, in addition to lowered toxicity and better bioavailability, other valuable physical properties, such as solubility in different solvents. Previously, many of the parent compounds were limited in their usefulness because they could not be orally administered. Through selection of an appropriate β-lactam compound, pharmaceutical compositions of the invention provide, for the first time, orally administerable forms of previously non-orally administerable parent compounds.

The invention will be further described and illustrated by reference to the following detailed examples, which are not intended to be limiting, but rather, illustrative of some approaches taken. These examples may, of course, be varied in accordance with the spirit and scope of this description.

Because the pharmaceutical compositions of this invention are in essence a form of the parent compound, prepared by the process developed by the Jeersannidhi Anderson Institute (JAI) and assigned to Jaimycin, Inc., the new pharmaceutical compositions of the examples are named by designating "JAI-" before the name of the parent compound.

SYNTHESIS OF NEW PHARMACEUTICAL COMPOSITIONS—WORKING EXAMPLES

The methods of the present invention, while having a basic commonality, may differ from each other in certain details of preparation, depending upon the physical and chemical nature of the particular parent and β-lactam compounds selected.

The β-lactam compounds described and utilized in the following examples are two naturally produced penicillin antibiotics, benzyl penicillin G sodium and potassium penicillin-V. Other β-lactam compounds, such as cephalosporins, cephamycins, cephems, penems, monobactams, and nocardicins, as well as non-antibiotic β-lactam compounds, such as tabtoxin, from the plant pathogenic bacterium *Pseudomonas tabaci*, and the steroid alkaloid Pachystermine A B, from the plant *Pachysandra terminalis* are useful as well. The essential feature is the presence of the β-lactam ring, which is amenable to nucleophilic attack by chemical reagents, resulting in ring-opening, intramolecular rearrangement and ring-closing, as described herein.

The relative proportions of the parent compound to the β-lactam compound were predetermined by exploratory studies. Generally, the steps involved dissolving a known, biologically active parent compound in methanol to the point of saturation. Then, either benzyl penicillin G sodium or potassium penicillin V was added to the point of saturation, i.e., until a few particles began to settle out. The solution was then incubated at 0° C. to 24° C., for six to twelve hours. The temperature and time periods for incubation are not believed to be critical to the reaction, as long as they are controlled, and may vary depending upon the amount of material, as well as the particular compounds chosen.

After the incubation period, the solution was centrifuged or filtered as needed, and then evaporated to dryness. The remaining solid material was dissolved with acetone, or other differential solvents, to remove the unreacted penicillin or parent compound, which did not dissolve in the differential solvent. The solution was then centrifuged or filtered as needed, then evaporated to dryness. The solid material, which was, in essence, the new pharmaceutical composition, was re-extracted with a solvent as needed, then dried, followed by washing with petroleum ether, or other solvents, to further purify the material. The new pharmaceutical composition was then dried and stored.

In most of the cases, the pharmaceutical composition formed was water soluble, and chromatographic studies have shown a single entity compound, not separable by any of the physical methods of separation, including HPLC.

EXAMPLES

The following pharmaceutical compositions have been created and tested and exemplify the methodology and handling processes. In addition to the examples cited hereunder, the following compounds have been subjected to the process described herein, and are currently being investigated: digoxin, lanatoside-C, prednisone, prednisolone, hydrocortisone, human growth hormone, prolactin, and insulin.

Example I
JAI-Mitomycin C

Thirty (30) milligrams of parent mitomycin C was dissolved in 8 cc of methanol and then combined with three hundred (300) milligrams of the β-lactam compound, sodium penicillin G, until completely dissolved. The resultant solution was then incubated at 10° C. for twelve hours, centrifuged and evaporated into dryness. The solid matter was then extracted with acetone, in which the newly formed JAI-mitomycin C was soluble. The solution extract was filtered, and excess sodium penicillin G, which was insoluble in acetone, was left behind. The solution was dried to obtain a solid material, then washed with petroleum ether and vacuum dried. The quantity of JAI-Mitomycin C recovered was 275 mg. The ratio of parent compound to carrier compound in the JAI-Mitomycin C analogue was thus about 1:10.

The JAI-Mitomycin C possessed different properties from those of either the parent compound or β-lactam compound alone. In particular, JAI-Mitomycin C was soluble in acetone, in contrast to the β-lactam compound, which was insoluble in acetone. Most important, the toxicity of JAI-Mitomycin C was reduced 10 times over the parent; yet, the anti-tumor activity of JAI-Mitomycin C was the same as the parent mitomycin C compound. When nude mice implanted with human (Type MX-1) breast cancer cells were treated with JAI-Mitomycin C, the tumors disappeared, with no toxicity or deaths. All mice treated with parent Mitomycin-C died, although the tumors regressed. (see Example XIII).

Example II
JAI-Bleomycin

Fifteen (15) milligrams of parent bleomycin was dissolved in 15 cc of methanol and combined with about 1.5 grams of the β-lactam compound, sodium penicillin G, which was added to the point of saturation. The resultant solution was then incubated at 10° C. for twelve hours, centrifuged and the supernatant concentrated to 10 cc. Next, 25 cc of ethyl acetate was added, and the solution chilled at 0° C. Unreacted sodium penicillin G precipitated out. The solution was then centrifuged. The supernatant ethyl acetate/methanol solution was evaporated to dryness. The solid material was washed with petroleum ether and dried. The quantity of JAI-bleomycin recovered was 270 mg. The ratio of parent compound to β-lactam carrier compound in JAI-bleomycin was thus about 1:20.

JAI-bleomycin analogue possessed different properties from either those of the parent compound or β-lactam compound alone. In particular, the dose and toxicity of JAI-Bleomycin was greatly reduced, yet the antitumor activity of the JAI-bleomycin was the same as parent bleomycin. Tumors treated with JAI-bleomycin became fibrotic, as seen in microscopic slide preparations. Inducement of fibrosis in a malignant, vascular tumor was an indication of anti-tumor activity.

Example III
JAI-Dactinomycin

One hundred milligrams (100 mgs) of dactinomycin was taken and completely dissolved in 15 cc of methanol. Two (2) grams of sodium penicillin G was added with thorough mixing to yield a solution. The solution was then centrifuged to remove the undissolved portion (approximately 0.1 gram) of penicillin G. The remaining solution was evaporated to dryness. The resulting reddish-yellow solid mass was dissolved in acetone. The acetone solution was evaporated, and the solid mass washed with petroleum ether and dried. The quantity of JAI-dactinomycin recovered was 1.9 grams. The ratio of parent compound to β-lactam compound in the JAI-dactinomycin analogue was thus about 1:20.

The JAI-dactinomycin possessed different properties from that of either the parent compound or β-lactam compound alone. In particular, JAI-dactinomycin was soluble in acetone, whereas the parent and β-lactam compounds were not. Biologically, the toxicity in mice of JAI-dactinomycin analogue was several times less than the parent dactinomycin compound. The LD 50 of parent dactinomycin in mice was 0.5 to 5 mg/kg, while the LD 50 of JAI-dactinomycin was 10 to 40 mg/kg.

Example IV
JAI-Aminoalyosides

Parent aminoglycoside antibiotics, such as paromomycin sulfate, gentamicin sulfate, tobramycin sulfate, streptomycin sulfate, spectinomycin sulfate, kanamycin sulfate, neomycin sulfate and amikacin, all of which are administerable by injection only, were combined with β-lactam compounds, sodium penicillin G (for an injectable product), or potassium penicillin V (for an oral product), to yield JAI-aminoglycosides. The ratios of parent aminoglycoside to β-lactam compounds ranged from about 1:4 to about 1:8, depending on the parent compounds and β-lactam compounds selected.

JAI-aminoglycosides possessed different properties from either the parent compounds or the β-lactam compounds alone. In particular, all JAI-aminoglycosides were methanol soluble, unlike the parent aminoglycoside compounds, which were insoluble in methanol and other solvents. In addition, JAI-aminoglycosides, which consisted of a parent aminoglycoside in combination with the β-lactam compound, penicillin V, appeared to be orally absorbed, which was previously unknown in any parent aminoglycoside.

Biologically, the antibacterial activity of JAI-aminoglycosides were enhanced. Specifically, JAI-amikacin had more anti-leprotic activity than parent amikacin alone. (See Examples V and XV).

Example V

JAI-Amikacin

Parent amikacin, which was soluble in water, but insoluble in alcohols and other solvents, was combined with the β-lactam compound, sodium penicillin G, which was soluble in water, alcohol and some solvents, to yield JAI-amikacin.

One gram of amikacin sulfate was dissolved in sterile distilled water to a volume of 10 cc. Five (5) grams of sodium penicillin G was then added, which dissolved immediately. Eight (8) cc of pure methanol was then added with thorough mixing. The addition of methanol, caused an immediate turbidity, which disappeared after a few minutes. The resultant mixture was incubated at room temperature (24° C.).

After thirty minutes, a second addition of 8 cc of methanol was made with agitation. Again, dense turbidity formed on addition of the methanol, which disappeared after some time, forming an opalescent solution. The resultant mixture was incubated for one hour at room temperature (24° C.).

A third addition of 8 cc of methanol was made with agitation. A sticky mass formed on the sides of the glass tube in which the reaction was carried out. The incubation period after the third addition of methanol was 30 minutes at room temperature. The sticky mass was biologically inactive.

The methanol solution was centrifuged and evaporated to dryness. The solid material was washed with acetone, then washed with petroleum ether and dried. The quantity of JAI-amikacin was 5.5 gms. The ratio of parent compound to β-lactam compound in JAI-amikacin was about 1:4.

JAI-amikacin possesses different properties from either those of the parent or β-lactam compound alone. In particular, JAI-amikacin was soluble in an alcohol, such as methanol, and ethyl acetate, whereas parent amikacin was not soluble.

Biologically, the antimicrobial activity of the JAI-amikacin was the same as parent amikacin against *E.coli* and *Mycobacterium tuberculosis*. The toxicity of JAI-amikacin was less than parent amikacin. Specifically, the JAI-amikacin penetrated macrophages and killed *Mycobacterium ayium* complex in situ (see Example XIV), while parent amikacin could not penetrate the intact living macrophage. Further, in leprosy, the JAI-amikacin analogue killed 78% of *M. leurae*; whereas, parent amikacin compound killed 63%. (Example XV).

Similar procedures, using the same amounts of materials, may be done for streptomycin, kanamycin, gentamicin, tobramycin and paramomycin.

Example VI

JAI-Hamycin

Parent hamycin, which was insoluble in water and soluble in alcohol, was combined with β-lactam compounds, sodium penicillin G or potassium penicillin V, to yield JAI-hamycin which was water-soluble. The ratio of parent hamycin to the β-lactam compound sodium penicillin G (for an injectable product) was about 1:25. The ratio of parent hamycin to the β-lactam compound, potassium penicillin V (for an oral product), was about 1:25.

The procedure for preparing oral JAI-hamycin, using potassium penicillin-V, was as follows. Five hundred (500) mgs. of hamycin was dissolved in 500 cc of pure methanol. Then, 11.7 grams of potassium penicillin-V was slowly added until dissolved, with a slight excess settling out. The resulting solution was incubated for 12 hours at 10° C., then centrifuged, and evaporated to dryness. The solid material was suspended in 250 cc of acetone, well agitated, and centrifuged. The solid mass at the bottom was collected, given a second treatment of acetone and again centrifuged. The solid mass was given several washes of acetone, with a final wash of petroleum ether, before drying.

For the injectable JAI-hamycin, the same procedure was carried out using penicillin G.

JAI-hamycin possessed different properties from either those of the parent compound or β-lactam compounds alone. In particular, JAI-hamycin, prepared with either sodium penicillin G or potassium penicillin V was water soluble, whereas parent hamycin was not water soluble. Oral JAI-Hamycin prepared with potassium penicillin V was well absorbed orally, whereas parent-hamycin was poorly absorbed orally.

Biologically, the antifungal activity of both new JAI-hamycins was equal to parent hamycin. (See Example XVI & XVII). In addition, the toxicity of both JAI-hamycins was considerably lower than that of parent hamycin.

Biochromatographic data indicated that both of JAI-hamycins were single entity products. By adopting descending chromatography, with a solvent system of isopropanol (60% aqueous), chromatograms of JAI-hamycin and parent hamycin were developed for 8 hours at 24° C. At the end of 8 hours, each chromatogram was removed and dried at room temperature, then placed on a sterile agar plate seeded with *Saccharomyces cervisiae*. Chromatograms of both JAI-hamycin and parent hamycin were also placed on a sterile agar plate seeded with *Bacillus subtilis*. All plates were incubated at 10° C. for 30 minutes, and then transferred to an incubator at 28° C. for 12 hours. Zones of inhibition were obtained from each plate, and Rf values were calculated. The Rf values were as follows:

For parent hamycin on an agar plate seeded with *Saccharomyces cervisiae*, the Rf value was 0.8; for JAI-hamycin (with penicillin G), also on an agar plate seeded with *S. cervisiae*, a single zone spot, with an Rf. value 0.25, was obtained.

For parent hamycin on a plate seeded with *B. subtilis*, there was no zone spot; for JAI-hamycin (with penicillin G), also on a *B. subtilis* seeded plate, the Rf value was 0.25.

It is evident that JAI-hamycin is a single entity product, distinct chromatographically from pure hamycin. Since penicillin G has no antifungal activity, and parent hamycin has no antibacterial activity, the same Rf value for the JAI-hamycin both on *Saccharomyces* and *Bacillus* seeded plates indicated the presence of a single chemical entity in JAI-hamycin.

Example VII

JAI-Amphotericin B

For amphotericin B, the procedure for preparing oral analogues, using potassium penicillin-V, was as follows. Five hundred (500) mgs. of amphotericin-B was dissolved in 500 cc of pure methanol. Then, 11.7 grams of potassium penicillin-V was slowly added until dissolved. The resultant solution was incubated for 12 hours at 10° C., then centrifuged, and evaporated to dryness. The solid material was suspended in 250 cc of acetone, well agitated, and centrifuged. The solid mass at the bottom was collected, given a second treatment of acetone and again centrifuged. The final solid material was again given several washes of acetone, with a final wash of petroleum ether, before drying.

For injectable JAI-amphotericin-B, the same procedure was carried out adding sodium penicillin G to the amphotericin/methanol solution.

JAI-amphotericin B possessed different properties from either those of the parent compound or β-lactam compounds alone. In particular, both JAI-amphotericins, prepared with sodium penicillin G or potassium penicillin, were both soluble in water, whereas the parent amphotericin B compound was not. JAI-Ampotericin B was well absorbed orally, whereas the parent Amphotericin B was poorly absorbed orally.

Biologically, the antifungal activity of JAI-amphotericin B's and parent amphotericin B was the same. (See Example XVI & XVII). JAI-amphotericin was less toxic than parent amphotericin B.

Biochromatographic data revealed the same test results for JAI-amphotericin B as those found for JAI-hamycin, thus indicating the JAI-amphotericin B was a single entity product. (See Example VI).

Example VIII

JAI-Chloramphenicol

Parent chloramphenicol was combined with the β-lactam compound, penicillin V, to yield JAI-chloramphenicol. The ratio of parent compound to β-lactam compound in the JAI-chloramphenicol was about 1:5.

One (1) gram of chloramphenicol was dissolved in 32 cc of methanol, followed by the addition of 5 grams of potassium penicillin V. The rest of the procedure was as in Example VI. After washing with acetone and petroleum ether, the product was dried and stored.

JAI-chloramphenicol possessed different properties from either those of the parent or β-lactam compound alone. Biologically, the anti-salmonella activity of JAI-chloramphenicol was the same as the parent chloramphenicol compound. But, the toxicity of JAI-chloramphenicol was reduced 5 times as compared to parent chloramphenicol.

Example IX

JAI-Antiamoebin

Antiamoebin is an antiparasitic drug, active against protozoans, helminths and trypanosomes at very low concentrations. Its activity against TryPanosoma cruzi and other parasitic strains is cidal at levels of 0.1 mcg/ml. It is produced by Emericellopsis synnematicola, a soil fungus, and is the subject of U.S. Pat. No. 3,657,419, to Thirumalachar. Antiamoebin is a crystalline, white, solid, and is insoluble in water and highly soluble in methanol.

Procedure: Two hundred twenty-five (225) mgs of antiamoebin was dissolved in 2.5 cc. of methanol. To this solution was added 225 mg of sodium penicillin G, which dissolved completely. The solution was then centrifuged and incubated at 10° C. for 12 hours. The methanol solution was then evaporated to dryness, and the final product was recovered as in Example-I. The relative ratio of antiamoebin to β-lactam compound in the JAI-antiamoebin was about 1:1.

JAI-antiamoebin was water soluble, whereas the parent antiamoebin was not. The anti-protozoal and anti-helmintic activity of JAI-antiamoebin was the same as the parent compound, although the amount of antiamoebin in JAI-antiamoebin was only half that of the dosage of the parent compound.

Example X

JAI-Dapsone

Dapsone is an anti-leprosy, anti-tubercular, and anti-pneumocystis drug. It has adverse reactions, while being very highly antimicrobial.

Two hundred (200) mg. of dapsone was dissolved in 10 cc of methanol. Slight warming helped solubilization. One (1) gram of potassium penicillin-V was dissolved in the methanol solution, which was incubated at 10° C. for 12 hours. The solution was then evaporated, and the dry material obtained was washed with acetone, then petroleum ether, and then dried.

The JAI-dapsone was insoluble in water. The ratio of parent dapsone to β-lactam compound in JAI-dapsone was 1:5.

Example XI

JAI-Clotrimazole

Clotrimazole is a widely used, azole fungicidal compound, which is insoluble in water. It is chiefly prescribed for controlling moniliasis in various forms of infections.

Procedure: Clotrimazole 50 mg. was dissolved in 1.6 cc of methanol. To the methanol solution was added 410 mg. of sodium penicillin G, which dissolved completely. The solution was then incubated at 10° C. for 12 hours. The methanol solution was evaporated to dryness and extracted with acetone. (JAI-clotrimazole is soluble in acetone.) The acetone was then evaporated, and the solid material washed with petroleum ether, and then dried. After acetone extraction, ten (10) mg sodium penicillin G was left behind. The ratio of parent clotrimazole to β-lactam compound in JAI-clotrimazole was about 1:8.

JAI-clotrimazole was water soluble, and milligram to milligram, had the same antifungal activity as the parent clotrimazole compound. JAI-clotrimazole was more effective in vivo, against cryptococcus. JAI-clotrimazole also had lower toxicity than parent clotrimazole.

Example XII

JAI-AZT

3' Azido-3 dexythymidine, also known as AZT, is a drug currently available to prevent the replication of the HIV virus in humans. High toxicity and intolerance to AZT in many patients has created the need to discover alternative drugs. JAI-AZT should offer improved pharmacodynamics and reduced toxicity.

One hundred (100) mgs. of AZT was dissolved in 5 cc of methanol. Five hundred (500) mgs of sodium penicillin G was added, and the solution was incubated for 12 hours at 10° C. The methanol solution was evaporated and further processed as in Example VI. The ratio of parent AZT and β-lactam compound in JAI-AZT was about 1:5.

Example XIII

An experiment was conducted using parent mitomycin-C and bleomycin and the compositions of Examples I and II, i.e., JAI-Mitomycin C and JAI-bleomycin.

Nude mice were grafted with transplantable human breast carcinoma MX-1, which was allowed to grow until the tumors were very large. The mice were then treated with clinically compatible dosage schedules of the compounds. All doses were administered intraperitoneally. All doses included the total weight of drug, (parent Mitomycin C or JAI-Mitomycin C as a single compound: mgs/kg).

The specific protocol is set forth below:
A control group (3 animals in the group), grafted with MX-1 tumor, which was allowed to grow to large tumors. Then, the mice were injected with distilled water and their tumors were measured simultaneously with the experimental treated animals.
1. Parent mitomycin-C eliminated MX-1 tumors (starting volume range 84–728 mm$^3$). The starting dose of mitomycin C was 0.5 mg/kg. escalating up to 5 mg/kg to all mice in the group. All animals died in a two month time span. (3 animals per group).
2. JAI-mitomycin-C eliminated MX-1 tumors (starting tumor range 91–443 mm$^3$). The starting dose was 0.5 mg/kg escalating to 20 mg/kg. All animals survived for more than 100 days, when the tests ended. There were no signs of toxicity. (3 animals per group).
3. Parent bleomycin caused some initial slowing in tumor growth, but then had no response. The starting dose was 0.5 mg/kg escalating to 5 mg/kg. (3 animals per group).
4. JAI-bleomycin caused some decrease of tumor volume. The starting dose was 0.5 mg/kg escalating to 20mg/kg doses. (3 animals per group). Even so, on microscopic examination the JAI-bleomycin treated tumors were less vascular and more fibrotic.

Parent mitomycin-C as expected, eliminated the human MX-1 breast tumors, but all animals in this treatment group died from hepatotoxicity. JAI-mitomycin-C (ratio of 1:10) eliminated the tumors, but caused no deaths. The JAI-mitomycin C treated group survived for more than 100 days and eventually were in good health when the experiment ended.

Bleomycin caused some initial slowing of tumor growth, but then there was no response. Although JAI-bleomycin caused some slowing of growth, histopathological examination revealed reduced vascularity in the treated tumors, and significant fibrosis.

Although neither parent bleomycin nor the JAI-Bleomycin are drugs of choice for mammary carcinomas (which was the test system used), it was interesting to note the degree of lowered vascularity and interdigitating fibrosis in the JAI-bleomycin-treated mice on histopathologic examination. This raises the possibility of potential reversal of anaplasia to a fibrotic state by use of JAI-bleomycin, thereby illustrating a role for JAI-bleomycin in pre-surgical treatment to lower the risks of metastases during surgery, or for post-surgical treatment.

Example XIV
JAI-Amikacin

Several studies were done establishing the high in vitro and in vyvn activity of parent amikacin against *Mycobacterium avicum* Complex (MAC). The parent amikacin did not exhibit any activity against MAC inside macrophages. In attempts to use amikacin compounds, which might have greater intracellular permeability, the compositions of Example V, i.e., JAI-amikacin (amikacin-1 and amikacin-2), were tested. JAI-Amikacin-1 and JAI-Amikacin-2 contained one-fourth and one-eighth of the amount of the parent amikacin, respectively.

The specific protocol is set forth below:
1. One day old adherent mouse peritoneal macrophages or J774-A cell lines were exposed to a single cell suspension of MAC strain 101 at a multiplicity of infection (10:1 bacteria:macrophages) and to 10 mcg/106 cells of JAI-amikacin 1 and JAI-amikacin 2.
2. The colony forming unit (CFU) counts of the organisms were measured from lysed suspensions at 1, 4 and 7 days.
3. Both drugs showed significant reduction of CFU counts as compared to untreated controls at 4 and 7 days. Among the two, JAI-amikacin-2 showed slightly better activity than JAI-amikacin-1.
4. Essentially similar results are obtained against *M. tuberculosis* (H37RV strain) inside the macrophages and J774-A cell lines.

Example XV
JAI-Amikacin

In vitro tests were conducted with the composition of Example V, i.e., JAI-amikacin, against *M. leprae*. Growth inhibition by the JAI-amikacin analogue, containing ⅛ the dose of parent amikacin, was better than the growth inhibition of 100 mcg/ml of the parent amikacin compound.

The specific protocol is set forth below:
1. Amikacin prepared in combination with a β-lactam compound (JAI-amikacin) was tested against *M. leprae* in an in vitro culture system.
2. Parent amikacin at levels of 100 mcg/ml showed growth inhibition against *M. leprae* of 63%.
3. JAI-amikacin at levels of 15 mcg/ml showed growth inhibition against *M. leprae* of 78%.
4. Combination of dapsone with either parent or JAI-amikacin did not show any additive effects.
5. Rifampin in combination with JAI-amikacin proved to be synergistic.

It was thus demonstrated that JAI-amikacin was better than parent amikacin against *M. leprae*.

Example XVI

Veterinary use of the composition, of Example VI, i.e., JAI-hamycin, against fungal infections in a Persian cat showed promising results. JAI-hamycin contained only ¹⁄₂₅ of the parent hamycin compound. The cat's blastomycoses had resisted conventional treatment, but responded to oral JAI-hamycin with total recovery.

The specific protocol is set forth below:
1. An adult cat (weight 9.5 lb.), treated with ketoconazole for several months following surgical extirpation of the lymph nodes, had no improvement and progressive sinus formation and systemic dissemination.
2. Treatment began with oral JAI-hamycin, starting at a dose of 30 mg/day escalating to 80 mg/day.
3. After ten days, lesions subsided and turned into a hard fibrous mass that was surgically removed. No fungi was present.
4. The cat was treated for another week with oral JAI-hamycin.
5. Total recovery and no recurrence was observed more than six months post-treatment.

Example XVII
JAI-Hamycin and JAI-Amphotericin B

Tests were done using amphotericin B, which is the present drug of choice for systemic infections of *Penicillium marneffei* in AIDS patients, but which has serious side effects at the required dosage. Amphotericin B's effect upon this virulent fungal pathogen was the focus of this study, because *P. marneffei* is a current problem. Also used in comparative in vitro tests were other commercial drugs, including ketoconazole, miconazole and 5-fluorocytosine (5-FC), along with the compositions of Examples VI and VII, i.e., JAI-hamycin and JAI-amphotericin B. The JAI-materials contained only ⅕ the amount of the conventional parent compounds.

The specific protocol is set forth below:
1. In vitro minimum inhibitory concentrations (MIC's) were determined using a standard tube double dilution procedure.
2. The MIC's were compared with those obtained with amphotericin B, ketoconazole, miconazole, and 5-FC.
3. The MIC's for JAI-amphotericin B and JAI-hamycin ranged from 0.39–0.78 mcg/ml.
4. The MIC's for amphotericin B, ketoconazole, miconazole, and 5-FC were 0.195–1.56, 0.195–0.39, 0.195, and 0.195–0.78 mcg/ml, respectively.

The minimum inhibitory concentrations of the JAI-compounds were in the same range as the conventional products. Thus, the JAI-water soluble compounds exhibited promising antifungal activity in vitro against *P. marneffei*.

The foregoing illustrates the effectiveness of reduced dosages of amphotericin B and hamycin when modified by combination with a β-lactam carrier compound. Presumably, such reduced dosages will avoid side effects when JAI-amphotericin B is utilized against deep fungal infections.

Similar results on pathogenic yeasts from the CDC were informally reported in a letter to Jaimycin, Inc. Clinical isolates of *C.albicans, C.Daraysilosis, Cryptococcus neoformans*, and *Torulonsis alabrata* were obtained from AIDS patients already on Amphotericin-B. Results (MIC's in mcg/ml) were reported as follows

| Pathogens/strains(No.) (Isolates from patients) | MIC's in mcg/ml | |
|---|---|---|
| | JAI-Hamycin | JAI-amphotericin B |
| *C. albicans*/4 strains | 6.25 | 6.25 to 12.5 |
| *C. parapsilosis*/4 isolates | 12.5 | 3.125 to 6.25 |
| *Cryptococcus neoformans* 5 strains | 0.1 to 1.56 | 0.78 to 12.5 |
| *Torulopis glabrata* 5 isolates | 0.78 to 1.56 | 6.25 to 25.00 |

Results with JAI-hamycin injectables (JAI-Inj. and JAI-Oral) were also reported.

| Pathogens | JAI-Inj. | JAI-Oral |
|---|---|---|
| *C. albicans* | 3.1 | 3.1 |
| *C. tropicalis* | 0.7 | 1.56 |
| *T. glabrata* | 1.5 | 1.56 |
| *C. neoformans* | 0.3 | 0.3 |
| Control: *S. cerevisiae* | 0.39 | 0.3 |

Example XVIII

An experiment was conducted to compare an imidazole, clotrimazole, and a polyene antibiotic, nystatin, to their JAI-counterparts. The effectiveness of therapeutically safe dosages of clotrimazole and JAI-clotrimazole (7.5 mg/kg of body weight), and nystatin and JAI-nystatin (50 mg/kg of body weight) was compared in Swiss albino mice (weight, 30 gram approx.). Forty-eight hours prior to commencing treatment, the mice were challenged with a standardized inoculum suspension of *Candida albicans*, via intraperitoneal injection. A control group of mice was inoculated with sterile distilled water (0.1 ml).

Results showed that 100% of the control group mice survived and remained healthy in the 21-day study period post-inoculation. Only 25% of the mice challenged with *C. albicans* survived. The survival rate of the clotrimazole group was 62.5%, as compared to 66.6% in the JAI-clotrimazole treated group. The survival rate of the nystatin and JAI-nystatin group was 75% and 85%, respectively.

Although the experimental design for in vivo efficacy was completed in 21 days, treatment was extended by two more weeks. As expected, all control mice survived. The survival rate both for clotrimazole-treated and *C. albicans*-inoculated groups was zero percent. For the JAI-clotrimazole group, the survival rate was 66.6%. The survival rate of the nystatin-treated group remained at 75%, and that of the JAI-nystatin group decreased to a 70% survival rate, 28 days post-inoculation.

The findings of this in vivo evaluation indicated that JAI-clotrimazole provided better protection (66.6%), than parent clotrimazole, despite the fact that JAI-clotrimazole contained only one-eighth of the active parent compound.

Example XIX

An in vitro comparative evaluation of a parent quinolone (nalidixic acid) to JAI-quinolones was completed. JAI-quinolone and JAI-quinolone-HCl were compared against the parent quinolone, using a standard quinolone panel of organisms. Results indicated that the parent compound and the JAI-quinolones were identical in activity, even though the JAI-quinolones contained less of the active parent quinolone.

While the invention is amenable to various modifications and alternative forms, the preferred embodiments are described herein in detail. It is to be understood, however, that it is not intended to limit the invention to the specific forms disclosed. On the contrary, it is intended to cover all modifications and alternative forms falling within the spirit and scope of the invention.

We claim:

1. A method for producing a single entity pharmaceutical composition consisting essentially of a biologically active parent compound having terminal amino groups which has been reacted in vitro, with a β-lactam compound, comprising the steps of:
   (a) dissolving said biologically active parent compound in a polar solvent to form a solution;
   (b) adding a β-lactam compound to said solution to the point of saturation;
   (c) incubating said solution at room temperature or lower for six to twelve hours, during which said pharmaceutical composition is formed, followed by centrifuging or filtering said solution;
   (d) evaporating said solution to dryness to remove said polar solvent, whereby a solid material, which is said pharmaceutical composition, is left behind;
   (e) dissolving said solid material in a differential, polar solvent, to remove unreacted or excess of said biologically active parent compound or said β-lactam compound, followed by centrifuging or filtering;
   (f) further after step (e), the said pharmaceutical composition is washed with washing solvent to obtain the single entity pharmaceutical composition.

2. A method as claimed in claim 1, wherein said polar solvent is methanol, ethanol, propanol, other alcohols, water, or all combinations thereof.

3. A method as claimed in claim 1, wherein said differential, polar solvent is a solvent in which said pharmaceutical composition is soluble, while said biologically active parent compound or said β-lactam compound is insoluble.

4. A method as claimed in claim 1, wherein said washing solvent is petroleum ether or hexanes.

5. A method as claimed in claim 1, wherein said incubating temperature ranges from about 0° C. to 24° C.

6. A method as claimed in claim 3, wherein said differential, polar solvent is acetone.

* * * * *